United States Patent [19]

Nakagawa et al.

[11] Patent Number: 5,321,022

[45] Date of Patent: Jun. 14, 1994

[54] COMPOSITIONS FOR PERCUTANEOUS ADMINISTRATION

[75] Inventors: Hiroshi Nakagawa, Nagaokakyo; Shoichi Harada, Osaka, both of Japan

[73] Assignee: Kanebo, Ltd., Tokyo, Japan

[21] Appl. No.: 22,382

[22] PCT Filed: Aug. 23, 1990

[86] PCT No.: PCT/JP90/01073
§ 371 Date: Apr. 24, 1991
§ 102(e) Date: Apr. 24, 1991

[87] PCT Pub. No.: WO90/03244
PCT Pub. Date: Mar. 21, 1991

Related U.S. Application Data

[63] Continuation of Ser. No. 674,339, Apr. 24, 1991, abandoned.

[30] Foreign Application Priority Data

Aug. 28, 1989 [JP] Japan .................... 1-220788

[51] Int. Cl.$^5$ ............................... A61K 31/55
[52] U.S. Cl. ..................... 514/218; 514/947
[58] Field of Search ................ 514/218, 947

[56] References Cited

U.S. PATENT DOCUMENTS 4,299,826 11/1981 Luedders .................. 514/947 X
4,430,343 2/1984 Iemura et al. .................. 424/250

FOREIGN PATENT DOCUMENTS 61-85328 4/1986 Japan .
1-207246 8/1989 Japan .

Primary Examiner—Jerome D. Goldberg
Assistant Examiner—Phyllis Spivack
Attorney, Agent, or Firm—Wegner, Cantor, Mueller & Player

[57] ABSTRACT

Compositions comprising emedastine and aliphatic monocarboxylic acid lower alkyl esters or aliphatic dicarboxylic acid di-lower alkyl esters for percutaneous administration are presented.

4 Claims, 1 Drawing Sheet

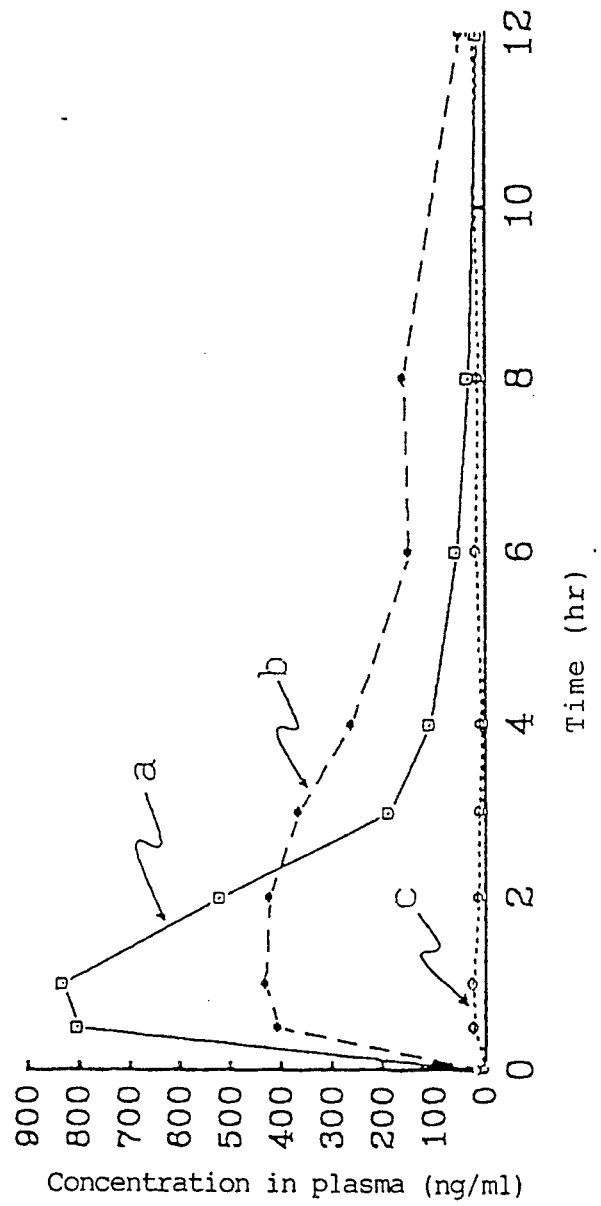

5,321,022

COMPOSITIONS FOR PERCUTANEOUS ADMINISTRATION

This application is a continuation of U.S. application Ser. No. 07/674,339, filed Aug. 24, 1991.

TECHNICAL FIELD

This invention relates to compositions for percutaneous administration of 1-(2-ethoxyethyl)-2-(hexahydro-4-methyl-1H-1, 4-diazepin-1-yl)-1H-benzimidazole.

PRIOR ART 1-(2-Ethoxyethyl)-2-(hexahydro-4-methyl-1H-1, 4-diazepin-1-yl)-1H-benzimidazole (hereinafter referred to as emedastine) is a compound of the following formula:

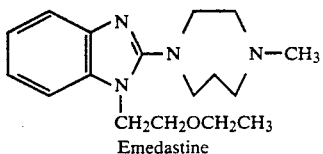

Emedastine which has a strong antihistaminic activity, and is useful for the prophylaxis and treatment of diseases caused by histamine such as allergic bronchial asthma, allergic dermatitis and allergic rhinitis, and the like (cf: U.S. Pat. No. 4430343).

The above mentioned U.S. Patent discloses that an ointment for percutaneous preparation containing emedastine or a pharmaceutically acceptable salt thereof can be prepared by using a conventional base, and in Examples thereof there is disclosed an ointment comprising emedastine difumarate and polyethylene glycol.

The above mentioned ointment comprising emedastine difumarate and polyethylene glycol is suitable, for example, for local treatment of allergic dermatitis, but in this ointment, the percutaneous absorption of emedastine is not satisfactory (cf: Experiments 1-2 described hereinbelow), and hence, the above mentioned ointment is not suitable enough for treatment based on the systemic action of emedastine, for example, for treatment of allergic bronchial asthma.

The present inventors have studied to provide compositions for percutaneous administration of emedastine based on the systemic action thereof, that is, compositions for percutaneous administration having a high percutaneous absorption ability of emedastine. An object of this invention is to provide compositions for percutaneous administration of emedastine having an excellent percutaneous absorption ability.

DISCLOSURE OF THE INVENTION

The present inventors have attempted various experiments, and found that when a composition comprising emedastine and aliphatic monocarboxylic acid lower alkyl esters or aliphatic dicarboxylic acid di-lower alkyl esters is percutaneously administered, the percutaneous absorption ability of emedastine is excellent, and have accomplished this invention.

That is, the object of this invention is to provide compositions for percutaneous administration of emedastine, which comprises emedastine and aliphatic monocarboxylic acid lower alkyl esters or aliphatic dicarboxylic acid di-lower alkyl esters.

The compositions of this invention can be prepared by mixing with stirring emedastine and the above mentioned esters at room temperature, if necessary, under warming.

The compositions of this invention can also be prepared by adding an aqueous solution of about one equivalent of an organic base (cf: triethanolamine, ethanolamine, etc.) or an inorganic base (cf: sodium hydroxide, sodium carbonate, etc.) to a mixture of a pharmaceutically acceptable salt of emedastine and the above mentioned esters, followed by mixing the mixture.

The aliphatic monocarboxylic acid lower alkyl esters include, for example, $C_1$–$C_4$ alkyl esters of an aliphatic saturated monocarboxylic acid having 6–18 carbon atoms or $C_1$–$C_4$ alkyl esters of oleic acid, preferably aliphatic saturated monocarboxylic acid $C_1$–$C_4$ alkyl esters wherein the total number of carbon atoms is 8–22, and oleic acid $C_1$–$C_4$ alkyl esters. These esters are, for example, ethyl octanoate, ethyl decanoate, ethyl hexanoate, ethyl laurate, ethyl myristate, isopropyl myristate, butyl myristate, isobutyl palmitate, butyl stearate, methyl oleate, ethyl oleate, butyl oleate, and the like.

The aliphatic dicarboxylic acid di-lower alkyl esters include, for example, di-($C_1$–$C_4$) alkyl esters of an aliphatic dicarboxylic acid having 6–10 carbon atoms, preferably ones wherein the total number of carbon atoms is 10–14, and are, for example, diethyl sebacate, diisopropyl adipate, diethyl suberate, diethyl adipate, and the like.

The above mentioned esters can be used either alone or in the form of a mixture of two or more esters. The amount thereof is usually 0.5–20 times by weight, preferably 2–10 times by weight as much as the amount of emedastine.

The above mentioned compositions are liquid at the ordinary temperature, and they can be used as a percutaneous preparation without any further treatment, but they can be also used by forming to preparations such as oily ointment, gels or creams by mixing thereof with a conventional pharmaceutical additive.

The oily ointment can be prepared by mixing the above mentioned composition with a conventional fatty and oily base such as vaseline, Plastibase ® (manufactured by Squibb Japan Inc.), Poloid ® (manufactured by Maruishi Seiyaku Co.), silicone fluid (manufactured by Dow Corning), and the like.

The gel preparations can be prepared by mixing the above mentioned composition with a water-soluble high molecular compound such as carboxymethyl cellulose, polyvinyl alcohol, carboxyvinyl polymer, and the like, and an appropriate amount of water.

The creams can be prepared by mixing the above mentioned composition with a higher alcohol (e.g. stearyl alcohol, etc.), a surfactant (e.g. sodium lauryl sulfate, etc.), vaseline, propylene glycol and an appropriate amount of water, and the like.

Besides, the above mentioned composition can be used by forming into a lotion or spray by dissolving in a volatile organic solvent (e.g. ethanol, isopropyl alcohol, acetone, etc.).

In addition, if necessary, to the above mentioned preparations can be added an antiseptic such as methyl parahydroxybenzoate, butyl parahydroxybenzoate, propyl parahydroxybenzoate, and the like.

The amount of emedastine in the above mentioned preparations containing the composition of this invention varies depending on the preparation forms, but is usually adjusted to the range of 0.1-10% by weight.

The above mentioned compositions, and oily ointments, gels, creams, lotions and sprays containing the said compositions can be percutaneously administered by spreading or spraying on the skin depending on the preparation form thereof.

The dosage varies depending on age, weight, and condition of patient, but it is usually administered in the dosage of 1-50 mg as emedastine per one administration and 1-3 times a day or once every two days to the skin of 2-50 cm$^2$ for an adult.

BRIEF DESCRIPTION OF THE DRAWINGS

FIG. 1 shows the periodical change of the concentration of emedastine in plasma when the composition of this invention or the composition of Reference Example was percutaneously administered to rabbits.

In the figure, the curve a shows the periodical change of the concentration of emedastine in plasma when the composition of Example 5 was percutaneously administered, and the curve b shows that when the composition of Example 8 was administered, and further the curve c shows that when the composition of Reference Example was administered.

THE BEST MODE FOR CARRYING OUT THE INVENTION

Hereinafter, this invention is illustrated by Examples and Reference Examples, but should not be construed to be limited thereto.

EXAMPLE 1

The liquid composition containing 20% by weight of emedastine was prepared by mixing emedastine (2 g) and ethyl octanoate (8 g) at room temperature.

EXAMPLES 2-11

The compositions of Examples 2-11 containing 20% by weight of emedastine were prepared in the same manner as described in Example 1 except that the esters as shown in Table 1 were used instead of ethyl octanoate.

TABLE 1

| Composition | Ester |
| --- | --- |
| Composition of Example 2 | Ethyl decanoate |
| Composition of Example 3 | Ethyl laurate |
| Composition of Example 4 | Ethyl hexanoate |
| Composition of Example 5 | Isopropyl myristate |
| Composition of Example 6 | Butyl stearate |
| Composition of Example 7 | Ethyl oleate |
| Composition of Example 8 | Diethyl sebacate |
| Composition of Example 9 | Diisopropyl adipate |
| Composition of Example 10 | Diethyl suberate |
| Composition of Example 11 | Diethyl adipate |

REFERENCE EXAMPLE 1

Emedastine (2 g) was added to the Japanese Pharmacopoeia macrogol (8 g) [prepared by mixing with warming polyethylene glycol 4000 (50 g) and polyethylene glycol 400 (50 g) at 65° C.], and the mixture was mixed at 65° C., and then cooled to the room temperature to give semisolid composition containing 20% by weight of emedastine.

REFERENCE EXAMPLE 2

The composition containing emedastine difumarate was prepared in the same manner as described in Reference Example 1 except that emedastine difumarate (3.5 g) was used instead of emedastine (2 g).

The percutaneous absorption ability of emedastine in the compositions of the above mentioned Examples and Reference Examples was tested by the following Experiments.

EXPERIMENTS 1

Test of penetration through the skin (diffusion cell method):

1) Test composition:
The compositions of Examples 1-11 and the compositions of Reference Examples 1-2

2) Test Method:
The abdominal skin of a Wister male rat was sheared, and peeled off one day thereafter. The skin was set onto a vertical diffusion cell (manufactured by Kercso Engineering, Ltd., effective area; 8 cm$^2$), and tested. The isotonic phosphate buffer (45 ml, pH 7.4) was used as a receptor solution. The test composition (1 g, 200 mg as emedastine) was administered to the donor side. The cell temperature was kept at 37° C., and 6 hours after the administration, the receptor solution (0.1 ml) was collected, and the concentration of emedastine thereof was determined by high performance liquid chromatography under the conditions as shown below.

Then, the amount of emedastine which had penetrated through the skin for the period of 6 hours was calculated based on the concentration of emedastine and the amount of the receptor solution.

Conditions for high performance liquid chromatography:

Column: Inertsil ODS (150 mm × 4.6 mm, 5 μm, manufactured by Gaschro Kogyo Inc.)

Eluent: A mixture of a solution [one part, prepared by dissolving disodium phosphate (3.9 g) and sodium lauryl sulfate (2.5 g) in water (1000 ml), followed by adjusting the pH value thereof to pH 2.4 with phosphoric acid] and acetonitril (one part)

Column Temperature: 40° C.

Flow rate: 1.4 ml/minute

Method of detection: measurement of absorbance at UV 280 nm

3) Test results:
The results are shown in Table 2.

TABLE 2

| Composition | Penetrated amount through the skin (mg) |
| --- | --- |
| Composition of Example 1 | 98.1 |
| Composition of Example 2 | 74.2 |
| Composition of Example 3 | 57.1 |
| Composition of Example 4 | 38.9 |
| Composition of Example 5 | 36.2 |
| Composition of Example 6 | 8.8 |
| Composition of Example 7 | 46.3 |
| Composition of Example 8 | 26.1 |
| Composition of Example 9 | 8.9 |
| Composition of Example 10 | 7.8 |
| Composition of Example 11 | 4.4 |
| Composition of Ref. Ex. 1 | 0.5 |
| Composition of Ref. Ex. 2 | 0.01 |

As is clear from the above results, the compositions of this invention are superior to the conventional compositions (the compositions of Reference Examples 1 and 2) in the penetration through the skin, that is, the percutaneous absorption ability of emedastine.

EXPERIMENT 2

Test of percutaneous absorption ability
1) Test compositions:
 The compositions of Examples 5 and 8, and the composition of Reference Example 1
2) Test method:
 The compositions of Example 5, Example 8 and Reference Example 1 (dosage: 11.3 mg/kg as emedastine) were administered to Japanese white rabbits (3 rabbits/group), which had previously fasted for 24 hours, by spreading thereof onto the left intra-auricular part (the side of ship-shaped cave) (15 cm$^2$). Subsequently, the blood was periodically collected from the right auricle veins, and thereto was added heparin and centrifuged to give the plasma. The concentration of emedastine in plasma was determined by gas chromatography in accordance with the method of Hamada et al.(cf: Chem. Pharm. Bull. Vol 34, page 1168, 1986).
3) Test results:
 The periodical change of concentration of emedastine in plasma (the average value of those of three rabbits in each group) is shown in FIG. 1. In FIG. 1, the curve a shows the periodical change of concentration of emedastine in plasma when the composition of Example 5 was percutaneously administered. The curve b shows that when the composition of Example 8 was administered. Further, the curve c shows that when the composition of Reference Example 1 was administered.

Moreover, when calculating the area under the curve formed by the concentration in plasma - time (AUC$_{0-12h}$), in the case that the composition of Example 5 was administered, it was 2104 ng.h/ml, and when the composition of Example 8 was administered, it was 2551 ng.h/ml, and further when the composition of Reference Example 1 was administered, it was 185 ng h/ml.

Thus, the compositions of this invention show the extremely excellent percutaneous absorption ability of emedastine in comparison with the compositions of Reference Examples in the tests using rabbits.

PROBABILITY OF INDUSTRIAL USE

As is clear from the above mentioned Experiments, the compositions of this invention show excellent penetration through the skin and the excellent percutaneous absorption ability of emedastine in comparison with the conventional compositions, and hence, the compositions of this invention are excellent as a composition for percutaneous administration of emedastine for the systemic action thereof.

Accordingly, the compositions of this invention are useful not only for the local treatment of allergic dermatitis but also for the systemic treatment of various allergic diseases caused by histamine.

We claim:
1. A composition for percutaneous administration consisting of a pharmacologically effective amount of 1-(2-ethoxyethyl)-2-(hexahydro-4-methyl-1H-1,4-diazepin-1yl)-1H-benzimidazole as an active ingredient and an ester selected from the group consisting of ethyl octanoate, ethyl decanoate, ethyl hexanoate, ethyl laurate, isopropyl myristate, ethyl oleate and diethyl sebacate wherein the amount of said ester is in the range of 0.5–20 parts by weight to one part by weight of the active ingredient.
2. The composition according to claim 1, wherein the amount of the said ester is in the range of 2–10 parts by weight to one part by weight of the active ingredient.
3. A composition according to claim 1 which is in the form of a liquid preparation.
4. A composition according to claim 1 which further includes an additive to form a preparation selected from the group consisting of oily ointments, gels, creams, lotions and sprays.

* * * * *

UNITED STATES PATENT AND TRADEMARK OFFICE
CERTIFICATE OF CORRECTION

PATENT NO. : 5,321,022

DATED : June 14, 1994

INVENTOR(S) : Hiroshi NAKAGAWA et al.

It is certified that error appears in the above-identified patent and that said Letters Patent is hereby corrected as shown below:

Column 6:
    Claim 1, line 21, "consisting of" should be corrected to --consisting essentially of--;

Claim 1, line 23, "diazepin-1yl" should be corrected to --diazepin-1-yl.--

Signed and Sealed this

Eleventh Day of October, 1994

Attest:

BRUCE LEHMAN

*Attesting Officer*     *Commissioner of Patents and Trademarks*